(12) United States Patent
Kong et al.

(10) Patent No.: US 8,669,068 B2
(45) Date of Patent: Mar. 11, 2014

(54) METHOD FOR DETERMINING PECTIN CONTENT IN PLANT SAMPLE

(75) Inventors: Haohui Kong, Guangdong (CN); Yifei Huang, Guangdong (CN); Baofeng Jin, Guangdong (CN)

(73) Assignee: China Tobacco Guangdong Industrial Co., Ltd., Guangdong (CN)

( * ) Notice: Subject to any disclaimer, the term of this patent is extended or adjusted under 35 U.S.C. 154(b) by 0 days.

(21) Appl. No.: 13/806,101

(22) PCT Filed: Dec. 12, 2011

(86) PCT No.: PCT/CN2011/083859
§ 371 (c)(1),
(2), (4) Date: Dec. 20, 2012

(87) PCT Pub. No.: WO2012/094934
PCT Pub. Date: Jul. 19, 2012

(65) Prior Publication Data
US 2013/0143249 A1    Jun. 6, 2013

(30) Foreign Application Priority Data
Jan. 13, 2011 (CN) .......................... 2011 1 0007055

(51) Int. Cl.
*C12Q 1/34* (2006.01)
*C12P 7/06* (2006.01)
*C12M 1/36* (2006.01)
*C12M 1/38* (2006.01)
*C12M 3/00* (2006.01)
*C12M 1/34* (2006.01)
*C12M 1/00* (2006.01)

(52) U.S. Cl.
USPC .......................... 435/18; 435/161; 435/286.7

(58) Field of Classification Search
USPC .......................................................... 435/18
See application file for complete search history.

(56) References Cited

FOREIGN PATENT DOCUMENTS

| CN | 101875703 A | 11/2010 |
| CN | 102033050 A | 4/2011 |
| SU | 556379 A1 | 4/1977 |

OTHER PUBLICATIONS

Kalapathy and Proctor "Effect of acid extraction and alcohol precipitation conditions on the yield and purity of soy hull pectin" 2001 Food Chemistry 73, 393-396.*
Sun et al. "Enzyme catalyzed change of antioxidants content and antioxidant activity of asparagus juice" 2007 J. Agric. Food Chem. 55, 56-60.*
Dalal et al. "A multipurpose immobilized biocatalyst with pectinase, xylanse and cellulase activities" 2007 Chemistry Central Journal 16, 1-5.*
Kintner and Van Buren "Carbohydrate Interference and its correction in Pectin Analysis Using m-hydroxydiphenyl method" 1982 Journal of Food Science 47, 756-759.*
Faravash, R.S. et al., The effect of pH, ethanol volume and acid washing time on the yield of pectin extraction from peach pomace, International Journal of Food Science & Technology 2007, No. 42, pp. 1177-1187.
Shang, Xuebo et al., Determination of Pectin Content in Citris Peel, Hunan Agricultural Sciences, 2010, No. 9, pp. 88-90.
Wang Peng et al., Improvement on Pretreatment for Determining Pectin in Tobacco with Enzymolysis-flowanalysis, Tobacco Science & Technology, 2009, No. 2, pp. 50-52.

* cited by examiner

*Primary Examiner* — John S Brusca
*Assistant Examiner* — Gerard Lacourciere
(74) *Attorney, Agent, or Firm* — Muncy, Geissler, Olds & Lowe, P.C.

(57) ABSTRACT

A method for determining pectin content in a plant sample includes: 1) adding an acidic alcohol solution to the plant sample, heating in a water bath and filtration; 2) soaking residue from step 1 with an acidic solution, heating in a water bath, a second filtration, bringing to volume after cooling and obtaining filtrate; 3) adding an acetic acid/sodium acetate buffer solution to residue of step 2, adding a pectinase solution, heating under vibration in a water bath, and a third filtration to obtain a filtrate; 4) adding an acetic acid/sodium acetate buffer solution and a pectinase solution to filtrate from step 2, heating the mixture under vibration in a water bath to obtain an enzymatic hydrolysate, adding filtrate obtained in step 3 to the enzymatic hydrolysate, bringing to volume, and obtaining a test solution; 5) drawing the test solution into a continuous flow analyzer to perform analysis.

14 Claims, 5 Drawing Sheets

METHOD FOR DETERMINING PECTIN CONTENT IN PLANT SAMPLE

FIELD OF THE INVENTION

The present invention relates to extracting plant components, and specifically, relates to the a method for determining pectin content in plant sample.

BACKGROUND OF THE INVENTION

In the determination of pectin content in plant, it is generally performed by chromogenic method. However, during the chromogenic determination, pigments will probably interfere the chromogenic determination result due to its optical absorbance, and in the meanwhile, sugars would react with chromogenic reagent to generate color substances, which would also cause interference to chromogenic determination. Therefore, during the determination process, pre-treatment should be performed including sugar removal, pigment removal, etc. . . . For determining pectin content in plant sample, conventional pre-treatment is as follows: heating the powdery plant sample with 80% ethanol solution to reflux for 1 hour followed by filtration to obtain residue for further extraction. This method is generally called as ethanol treatment method, However, the deficiency of such ethanol treatment method is that such method could only remove the micromolecular water-soluble sugars, and has certain limitation in pigment extraction. Furthermore, when treating the residue, acid solution is sometimes required, which makes the extracted polysaccharides hydrolyzed and thus extracted. In the meanwhile, cell walls are broken due to the effect of acid, which makes the previously dissolved pigment be extracted and thus influences the final results of determination. After pre-treating process, the resulting sample is determined. Existing determination method is gravimetric method. Since pectin is not polymerized from pure galacturonic acid, when determining by gravimetric method, neutral sugars and alpha-L-(1→2) rhamnoses on the branched chains, as well as methylated groups and acetylated groups, are simultaneously precipitated, the weight thereof is inevitably more than the cumulated amount of galacturonic acid. Therefore, the determination results of gravimetric method could not imply the galacturonic acid content in sample, that is, it could not imply the content of galacturonic acid branched chain skeleton used for the characterization of pectin in sample.

SUMMARY OF THE INVENTION

Provided is a method for determining pectin content in plant sample, to obtain an accurate determination result, overcoming the deficiencies of the prior art.

The method provide in the present invention for determining pectin content in plant sample, comprises steps of:

1) adding an acidic alcohol solution to the plant sample, followed by a heating in a water bath and then a first filtration;
2) soaking a filtered residue obtained from the first filtration with an acid solution, followed by a heating in a water bath and then a second filtration, then bringing to volume after cooling, obtaining a filtrate for later use;
3) adding an acetic acid/sodium acetate buffer solution to treat a filtered residue obtained from the second filtration, then adding a pectinase solution and heating the resulting mixture under vibration in a water bath, followed by a third filtration to obtain a filtrate for later use;
4) adding an acetic acid/sodium acetate buffer solution and a pectinase solution in sequence to the filtrate obtained in step 2) and heating the resulting mixture under vibration in a water bath to obtain an enzymatic hydrolysate, then adding the filtrate obtained in step 3) to the enzymatic hydrolysate followed by bringing to volume, obtaining a test solution; and
5) drawing the test solution into a continuous flow analyzer to perform analysis, wherein the test solution is reacted with a strong-acid decomposing reagent drawn into the continuous flow analyzer, to form furfurine derivatives, which is further reacted with an chromogenic reagent, followed by a determination under a wavelength of 490-540 nm.

Preferably, the acidic alcohol solution in step 1) has a alcohol concentration of 60%-80% (v/v) and a hydrogen ion concentration of 0.005 mol/L-0.02 mol/L; wherein said acidic alcohol solution is added at a ratio of 50 mL-200 mL acidic alcohol solution: 1 g sample.

Preferably, the heating under vibration in a water bath in step 1) is conducted under 80° C.-100° C. for 10 min-1 h.

Preferably, said acidic solution is hydrochloric acid at a concentration of 0.05 mol/L-0.1 mol/L; the heating to reflux in a water bath is conducted under 80° C.-100° C. for 30 min-2 h; the volume of the filtrate after bringing to volume is 200 mL-250 mL for every 1 g plant sample.

Preferably, the acetic acid/sodium acetate buffer solution and the pectinase solution are added at a ratios of 1 g plant sample: 15 mL-20 mL buffer solution: 1 mL-2 mL pecinase solution; wherein the enzymatic activity per 1 mL pectinase solution is above 300 enzymatic active unit; the heating under vibration in a water bath is conducted under 40° C.-60° C. for 1 h-2 h.

Preferably, every 1 mL filtrate is added with 15-20 mL buffer solution and 1-2 mL pectinase solution; wherein the enzymatic activity per 1 mL pectinase solution is above 300 enzymatic active unit; the heating under vibration in a water bath is conducted under 40° C.-60° C. for 1 h-2 h.

Preferably, in step 5), the test solution is mixed with the strong-acid decomposing reagent via a helix tube and is heated during reaction with the strong-acid decomposing reagent, followed by a cooling.

Preferably, said plant sample is powdery.

Preferably, the plant sample in step 1) is added with an acidic alcohol solution and stirred to become slurry before heating to reflux in a water bath, if said plant sample has a large volume.

Preferably, said the chromogenic reagent is p-hydroxydiphenyl solution, wherein said p-hydroxydiphenyl solution is formed by components at a ratio of 1000 mL distilled water:300-500 mg p-hydroxydiphenyl:3 g-5 g sodium hydroxide.

Preferably, the strong-acid decomposing reagent is sulfuric acid containing sodium tetraborate, wherein 3 g-6 g sodium tetraborate is dissolved in 1000 mL sulphuric acid solution at a concentration of 92%-99% concentrated.

Preferably, the test solution and the strong-acid decomposing reagent is reacted at a temperature in the range of 90° C.-99° C.

Preferably, said cooling is performed in the cooling tube with 20 turns-50 turns.

Preferably, the pectinase solution in step 3) and/or step 4) are/is at a volume concentration of 300 u/mL-600 u/mL.

Compared to the prior art, the present invention has the following advantages:

1. Since acidic alcohol solution treatment is employed in step 1) to replace alcohol solution treatment in the prior art, it bring higher sugar removal rate and thus save treatment time. In addition, it is able to save the acid solution soaking time and heating time. In the meanwhile, it no longer requires a great number of dilution work as required in the prior art which is only suitable for low concentration determination, and thus reduces steps of bringing to volume and therefore is highly efficient with simple process.

2. Since the test solution obtained after treatment is determined by continuous flow method, the test solution is drawn into the continuous flow analyzer and reacted with a strong-acidic decomposing reagent which will rot and decompose the pectin and transform it into derivants that is chromogenic, and thus is helpful to optical determination with simplified process.

DETAILED DESCRIPTION OF THE EMBODIMENTS

With regard to the following embodiments, the present invention will be described in detail in order to make the purposes and technical solutions thereof more clear.

Figure 1:
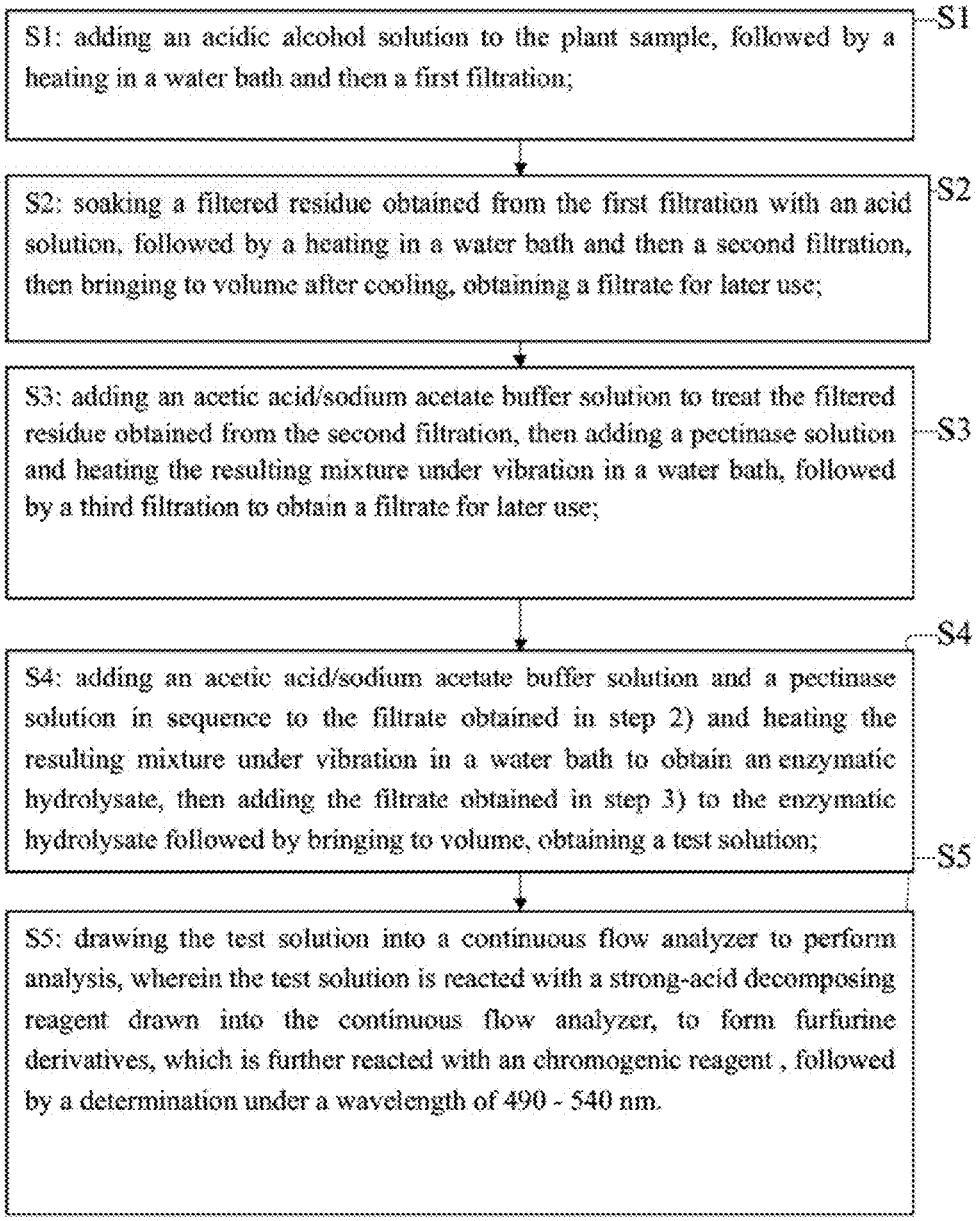
FIG. 1 refers to the flow chart of the continuous flow method for determining pectin content in plant according to the present invention.

With reference to FIG. 1, the method for determining pectin content in plant sample in the present invention, comprises steps of:
S1. Adding an acidic alcohol solution to the plant sample, followed by a heating in a water bath and then a first filtration;
S2. Soaking a filtered residue obtained from the first filtration with an acid solution, followed by a heating in a water bath and then a second filtration, then bringing to volume after cooling, obtaining a filtrate for later use;
The residue obtained from the second filtration is then washed with acid solution for several times, so that the filtrate absorbed by the residue may be greatly removed;
After finishing this step, most pectin component will be extracted into the filtrate;
S3. Adding an acetic acid/sodium acetate buffer solution to treat a filtered residue obtained from the second filtration, then adding a pectinase solution and heating the resulting mixture under vibration in a water bath, followed by a third filtration to obtain a filtrate for later use;
After finishing this step, the pectin extracted from the residue is extracted into the extract, and decomposed into galacturonic acid;
S4. Adding an acetic acid/sodium acetate buffer solution and a pectinase solution in sequence to the filtrate obtained in step 2) and heating the resulting mixture under vibration in a water bath to obtain an enzymatic hydrolysate, then adding the filtrate obtained in step 3) to the enzymatic hydrolysate followed by bringing to volume, obtaining a test solution;

After this step, the pectin in the extract of acid solution is sufficiently hydrolyzed into galacturonic acid, and mixed with the remaining pectin extract in the residue, so that the pectin obtained from extraction could be sufficiently collected to obtain the test solution, in order to make the final determination result more accurate;
S5. Drawing the test solution into a continuous flow analyzer to perform analysis, wherein the test solution is reacted with a strong-acid decomposing reagent drawn into the continuous flow analyzer, to form furfurine derivatives, which is further reacted with an chromogenic reagent, followed by a determination under a wavelength of 490-540 nm.

The reaction between the test solution and the strongly acidic decomposing reagent makes the pectin rotted and converted into chromogenic derivatives, which is convenient for the spectrometric determination;

Wherein, said chromogenic reagent is p-hydroxydiphenyl solution, the forming of said p-hydroxyphenyl solution is that 300 mg-500 mg, preferably 400 mg, of p-hydroxydiphenyl, and 3 g-5 g, preferably 4 g, of sodium hydroxide, are dissolved in 1000 mL of distilled water.

Wherein, said strong-acid decomposing reagent is sulphuric acid solution containing sodium tetraborate, wherein the forming of sulphuric acid solution containing sodium tetraborate is that 3-6 g, preferably 4.8 g, of sodium tetraborate is dissolved in 1000 mL of 92%-99% sulphuric acid.

Wherein, said strong-acid decomposing reagent is injected into the continuous flow analyzer by using parallel system with two or three pump pipes; the flow within each single pump pipe is controlled at the range of 0.6 ml/min-1.2 ml/min, the total flow is controlled at the range of 1.6 ml/min-3.0 ml/min. The ratio of the flow of strong-acid decomposing reagent to the sample injection volume is at the range of 13.0:1-30:1, and preferably, 16:1-20:1. This kind of system is used, to overcome the problem that said strong-acid decomposing reagent with high viscosity is difficult to flow within the pipeline of the flow analyzer.

The present invention will be further described with reference to the following specific examples.

Embodiment 1

1) The acidic alcohol solution with 60% (v/v) ethanol and 0.01 mol/L hydrochloric acid is added into the plant sample, heated in a water bath at 90° C. to reflux for 20 minutes, and then subjected to the first filtration;
2) The residue obtained from the first filtration is soaked with 0.05 mol/L hydrochloric acid solution, heated in water bath at 90° C. to reflux for 30 minutes, and then subjected to the second filtration and diluted to the metered volume of 250 mL after cooling to obtain the filtrate for further use;
3) 20 mL 0.1 mol/L acetic acid/sodium acetate buffer solution at pH 4.0 is added into the residue obtained from the second filtration, and 1 mL 300 u/mL pectinase solution is subsequently added thereinto, then the resulting mixture is heated and vibrated for 1 hour in low-temperature water bath at 55° C., and then subjected to the third filtration to obtain the filtrate for further use;
4) 1 mL filtrate obtained from step 2) is transferred, then 20 mL 0.1 mol/L acetic acid/sodium acetate buffer solution at pH 4.0 and 1 mL 300 u/mL pectinase solution added thereinto in sequence, then the mixture is heated and vibrated for 1 hour in low-temperature water bath at 55° C. to obtain enzymatic hydrolysate solution, followed by the adding of the filtrate obtained from step 3) into the enzymatic hydrolysate solution, and a dilution to the metered volume of 100 mL with 0.1% (w/w) benzoic acid solution, to obtain the test solution;

5) The test solution (test sample), is drawn into continuous flow analyzer, passed through the helix tube and mixed with the sulphuric acid solution containing sodium tetraborate decahydrate which is drwan into the continuous flow analyzer, then heated to 90° C. The test solution is reacted with the sulphuric acid solution containing sodium tetraborate decahydrate, decomposed and converted into furfurine derivatives, then mixed with introduced chromogenic reagent via helix tube after cooling, to be reacted with said chromogenic reagent to generate color, and then determined at the wavelength of 500 nm.

Wherein, all filtering processes require glass fiber filters, instead of common filters. Other filters without plant fibers can also be used for instead.

Figure 2:
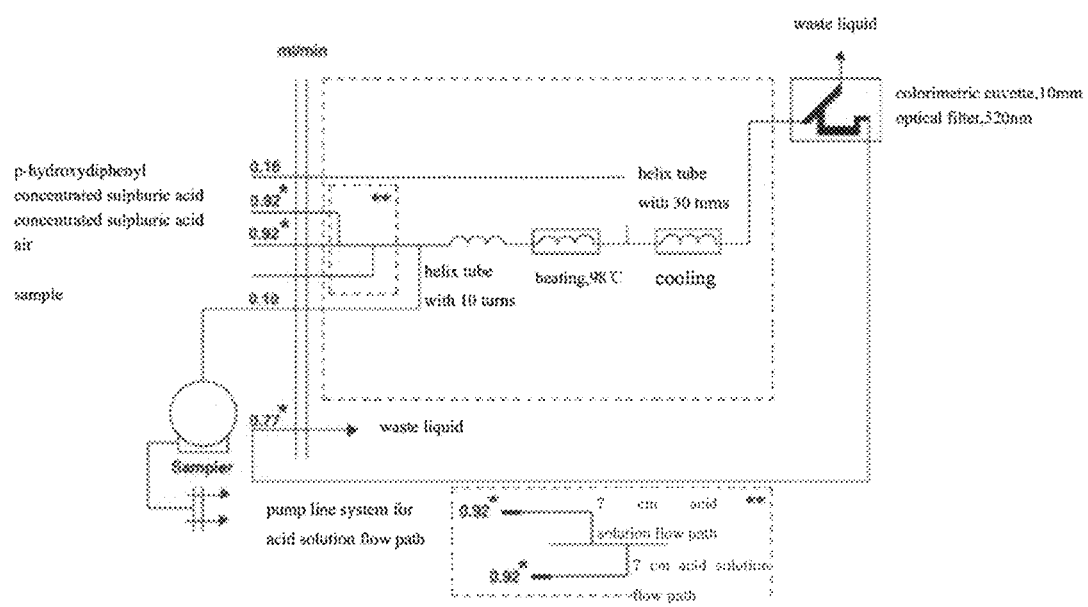
FIG. 2 refers to the flow chart of the determination by continuous flow analyzer according to the present invention.

Wherein, the detection process in step 5) can be referred to FIG. 2.

Wherein, the chromogenic reagent in step 5) is p-hydroxydiphenyl solution, the forming of said p-hydroxyphenyl solution is that 400 mg p-hydroxydiphenyl and 4 g sodium hydroxide are dissolved in 1000 mL distilled water.

Wherein, with respect to the sulphuric acid solution containing sodium tetraborate, the forming thereof is that 3.5 g sodium tetraborate is dissolved in 1000 mL 93% concentrated sulphuric acid.

Wherein, with respect to the heater used for heating in the step 5), the internally installed helix tube for heating thereof is of 64 turns.

Wherein, the cooling process in step 5) is performed in a water bath, and the cooling tube is of 30 turns (the inlet port for cooling water is directly connected to the faucet, the settings of the flow of cooling water and the turns of helix tube are such that the temperature within the pipeline after cooling stands close to room temperature).

Embodiment 2

1) The acidic alcohol solution with 80% (v/v) ethanol and 0.01 mol/L hydrochloric acid is added into the plant sample, heated in a water bath at 89° C. to reflux for 25 minutes, and then subjected to the first filtration;
2) The residue obtained from the first filtration is soaked with 0.1 mol/L hydrochloric acid solution, heated in a water bath at 92° C. to reflux for 30 minutes, and then subjected to the second filtration to obtain the filtrate for further use;
3) 20 mL 0.1 mol/L acetic acid/sodium acetate buffer solution at pH 4.0 is added into the residue obtained from the second filtration, 1 mL 400 u/mL pectinase solution is subsequently added thereinto, then the resulting mixture is heated and vibrated for 1.5 hour in low-temperature water bath at 50° C., and then subjected to the third filtration to obtain a filtrate for further use;
4) 1 mL filtrate obtained from step 2) is transferred, then 20 mL 0.1 mol/L acetic acid/sodium acetate buffer solution at pH 4.0 and 1 mL 400 u/mL pectinase solution are added thereinto in sequence, then the resulting mixture is heated and vibrated for 1 hour in low-temperature water bath at 55° C. to obtain enzymatic hydrolysate solution, followed by the adding of the filtrate obtained from step 3) into the enzymatic hydrolysate solution, and then a dilution to the metered volume of 250 mL with 0.1% (w/w) benzoic acid solution, to obtain the test solution;
5) The test solution (test sample), is drawn into continuous flow analyzer, passed through the helix tube and mixed with the sulphuric acid solution containing sodium tetraborate decahydrate which is drawn into the continuous flow analyzer, then heated to 95° C. The test solution is reacted with the sulphuric acid solution containing sodium tetraborate decahydrate, decomposed and converted into furfurine derivatives, then mixed with introduced chromogenic reagent via helix tube after cooling, to be reacted with said chromogenic reagent to generate color, and then determined at the wavelength of 530 nm.

Wherein, the detection process in step 5) can be referred to FIG. 2.

Wherein, the chromogenic reagent in step 5) is p-hydroxydiphenyl solution, the forming of p-hydroxyphenyl solution is that 300 mg p-hydroxydiphenyl and 3 g sodium hydroxide are dissolved in 1000 mL distilled water.

Wherein, with respect to the sulphuric acid solution containing sodium tetraborate, the forming thereof is that 3 g sodium tetraborate is dissolved in 1000 mL 92% concentrated sulphuric acid.

Wherein, with respect to the heater used for heating in the step 5), the internally installed helix tube for heating thereof is of 35 turns.

Wherein, the cooling process in step 5) is performed in a water bath, and the cooling tube is of 25 turns.

Embodiment 3

1) The acidic alcohol solution with 80% (v/v) ethanol and 0.005 mol/L hydrochloric acid is added into the plant sample, heated in a water bath at 88° C. to reflux for 35 minutes, and then subjected to the first filtration;
2) The residue obtained from the first filtration is soaked with 0.08 mol/L hydrochloric acid solution, heated in a water bath at 89° C. to reflux for 1 hour, and then subjected to the second filtration to obtain the filtrate for further use;
3) 25 mL 0.1 mol/L acetic acid/sodium acetate buffer solution at pH 4.0 is added into the residue obtained from the second filtration, and 1 mL 400 u/mL pectinase solution is subsequently added thereinto, then the resulting mixture is heated and vibrated for 2 hour in low-temperature water bath at 45° C., and then subjected to the third filtration to obtain the filtrate for further use;
4) 1 mL the filtrate obtained from step 2) is transferred, then 25 mL of 0.1 mol/L acetic acid/sodium acetate buffer solution at pH 4.0 and 1 mL of 400 u/mL pectinase solution added thereinto in sequence, then the mixture is heated and vibrated for 2 hour in low-temperature water bath to obtain enzymatic hydrolysate solution, followed by the adding of the filtrate obtained from step 3) into the enzymatic hydrolysate solution, and a dilution to the metered volume of 250 mL with 0.1% (w/w) benzoic acid solution, to obtain the test solution;
5) The test solution (test sample) is drawn into continuous flow analyzer, passed through the helix tube and mixed with the sulphuric acid solution containing sodium tetraborate decahydrate which is drawn into the continuous flow analyzer, then heated to 96° C. The test solution is reacted with the sulphuric acid solution containing sodium tetraborate decahydrate, decomposed and converted into furfurine derivatives, then mixed with introduced chromogenic reagent via helix tube after cooling, to be reacted with said chromogenic reagent to generate color, and then determined at the wavelength of 520 nm.

Wherein, the detection process in step 5) can be referred to FIG. 2.

Wherein, the chromogenic reagent in step 5) is p-hydroxydiphenyl solution, the forming of said p-hydroxyphenyl solution is that 360 mg p-hydroxydiphenyl and 5 g sodium hydroxide are dissolved in 1000 mL of distilled water.

Wherein, with respect to the sulphuric acid solution containing sodium tetraborate, the forming thereof is that 6 g sodium tetraborate is dissolved in 1000 mL 94% concentrated sulphuric acid.

Wherein, with respect to the heater used for heating in the step 5), the internally installed helix tube for heating thereof is of 35 turns.

Wherein, the cooling process in step 5) is performed in a water bath, and the cooling tube is of 40 turns.

Embodiment 4

1) The acidic alcohol solution with 80% (v/v) ethanol and 0.02 mol/L hydrochloric acid is added into the plant sample, firstly stirred into a slurry, then heated in a water bath at 91° C. to reflux for 21 minutes, and then subjected to the first filtration;
2) The residue obtained from the first filtration is soaked with 0.010 mol/L hydrochloric acid solution, heated in water bath at 86° C. to reflux for 1 hour, and then subjected to the second filtration to obtain the filtrate for further use;
3) 25 mL 0.1 mol/L acetic acid/sodium acetate buffer solution at pH 4.0 is added into the residue obtained from the second filtration, 1 mL 300 u/mL pectinase solution is subsequently added thereinto, then the resulting mixture is heated and vibrated for 1.8 hour in low-temperature water bath at 48° C., and then subjected to the third filtration to obtain the filtrate for further use;
4) 1 mL filtrate obtained from step 2) is transferred, then 25 mL of 0.1 mol/L acetic acid/sodium acetate buffer solution at pH 4.0 and 1 mL of 300 u/mL pectinase solution are added thereinto in sequence, then the resulting mixture is heated and vibrated for 1 hour in low-temperature water bath to obtain enzymatic hydrolysate solution, followed by the adding of the filtrate obtained from step 3) into the enzymatic hydrolysate solution, and a dilution to the metered volume of 250 mL with 0.1% (w/w) benzoic acid solution, to obtain the test solution;
5) The test solution (test sample), is drawn into continuous flow analyzer, passed through the helix tube and mixed with the sulphuric acid solution containing sodium tetraborate decahydrate which is drawn into the continuous flow analyzer, then heated to 93° C. The test solution is reacted with the sulphuric acid solution containing sodium tetraborate decahydrate, decomposed and converted into furfurine derivatives, then mixed with introduced chromogenic reagent via helix tube after cooling, to be reacted with said chromogenic reagent to generate color, and then determined at the wavelength of 490 nm.

Wherein, the detection process in step 5) can be referred to FIG. 2.

Wherein, the chromogenic reagent in step 5) is p-hydroxydiphenyl solution, the forming of said p-hydroxyphenyl solution is that 400 mg of p-hydroxydiphenyl and 4.5 g sodium hydroxide are dissolved in 1000 mL distilled water.

Wherein, with respect to the sulphuric acid solution containing sodium tetraborate, the forming thereof is that 5 g sodium tetraborate is dissolved in 1000 mL 95% concentrated sulphuric acid.

Wherein, with respect to the heater used for heating in the step 5), the internally installed helix tube for heating thereof is of 64 turns.

Wherein, the cooling process in step 5) is performed in a water bath, and the cooling tube is of 30 turns.

The effects of the method for determining pectin content in plant sample of the present invention will be demonstrated by the following experiments.

1. The Interference Caused by the Background Color of Extracted Test Sample

Pretreatment: 0.1 g powdered plant sample is accurately weighed, 100 mL hydrochloric acid-ethanol solution with the hydrogen ion concentration of 0.01 mol/L and the alcohol content of 80% is added thereinto, then heated to reflux for 20 minutes in water bath at 90° C., and then filtered to remove sugar components and pigments. The residue is provided for the further extraction of the testing components.

The acid solution treatment program and the enzymatic hydrolyzation and extraction program are the same as those mentioned above, and thus are not described in detail hereinafter.

Experimental program: the test solution, i.e., the extract with the extracted pectin, is injected into the continuous flow analyzer as test sample. In the absence of chromogenic reagent, the solution which is mixed with other solvents except the chromogenic reagent, flow from said analyzer and is analyzed by UV-visible spectrometer for its absorbance. Determination results are shown in Table 1.

TABLE 1

The results of absorbance scanning of test samples flowing through the analyzer

| | Absorbance value at different wavelengths, A | | | | |
|---|---|---|---|---|---|
| Sample | 500 nm | 510 nm | 520 nm | 530 nm | 540 nm |
| 1# | 0.0003 | 0.0002 | 0.0003 | 0.0006 | 0.0011 |
| 2# | 0.0005 | 0.0006 | 0.0008 | 0.0011 | 0.0013 |

According to the data in Table 2, there is an extremely low amount of pigments in the test solution. The background color of the test solution causes little interference to the chromogenic determination at around the wavelength scope employed in pectin determination, and thus would not cause interference to the absorbance determination. It is indicated that the acidic alcohol solution achieve satisfactory results in removing pigment.

2. Defining the Wavelengths for Determination

Experimental program 1: 1 mL galacturonic acid standard solution (with galacturonic acid concentration of 50 mg/L) is placed into a 20 mL test tube with plug; 6 mL sodium tetraborate-sulphuric acid solution is added thereinto; after cooling, 1 mL m-hydroxydiphenyl solution, as a chromogenic reagent, is added thereinto by pipettor; the mixture is then homogenized and ultrasonically vibrated for 5 min for degassing. In the meanwhile, 1 mL distilled water is parallelly prepared as blank solution for zero setting. Scanning is performed within the wavelength range of 350 mm-800 nm by UV-visible spectrometer. The scanning result is shown in FIG. 3.

Figure 4:
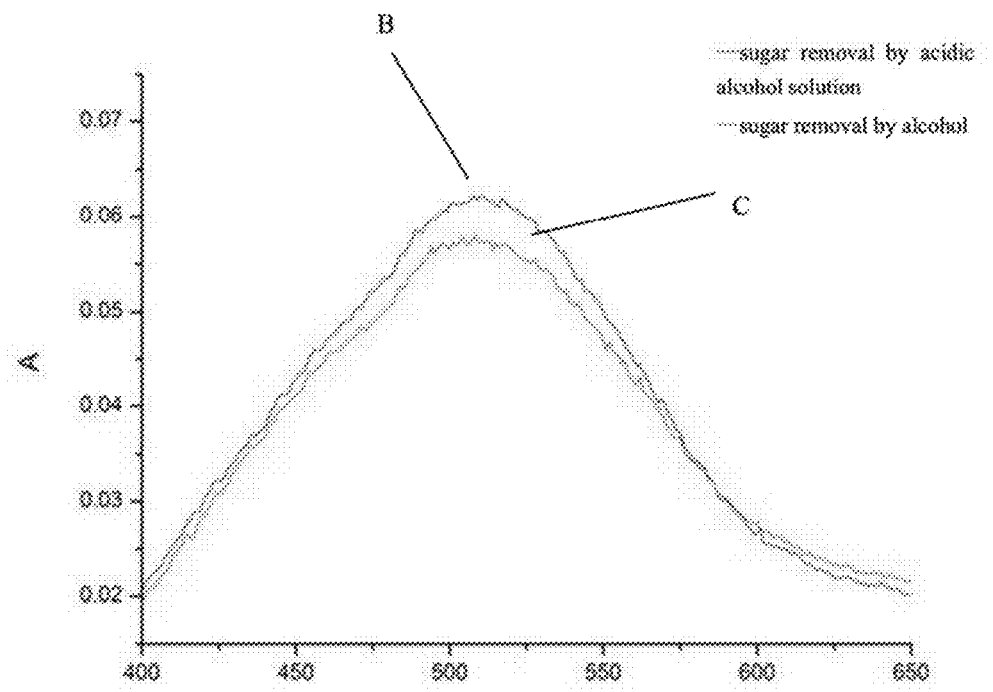
FIG. 4 refers to the scanning absorbance spectrum of sample extract after the chromogenic reaction
FIG. 5 refers to a first absorbance spectrum scanned by analyzer.

Experimental program 2: according to the method mentioned in the previous example, the pectin is extracted to obtain the test solutions. 1 mL of each of the two different test solutions is respectively placed into a 20 mL test tube with plug; 6 mL sodium tetraborate-sulphuric acid solution is respectively added thereinto; after cooling, 1 mL m-hydroxydipheny solution is respectively added thereinto; the mixture is then homogenized and ultrasonically vibrated for 5 for degassing. In the meanwile, 1 mL distilled water is parallelly prepared as blank solution for zero setting. Scanning is performed within the wavelength range of 400-650 nm by UV-visible spectrometer in order to determine the maximum absorption wavelength. The scanning result is shown in FIG. 4.

Figure 3:
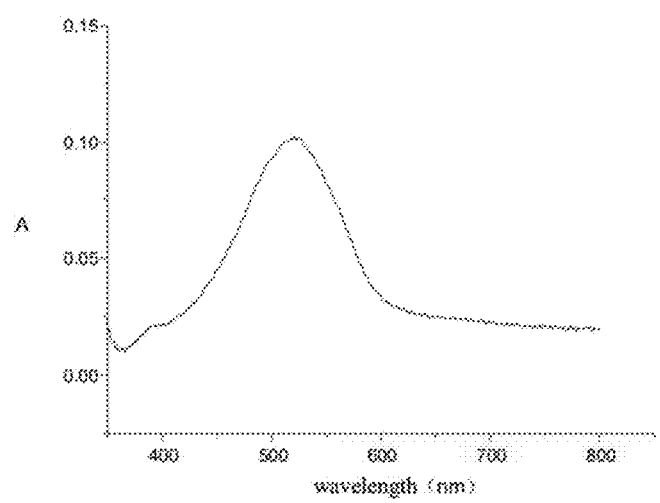
FIG. 3 refers to the scanning absorbance spectrum of galacturonic acid standard solution after the chromogenic reaction.

Acoording to FIG. 3, after chromogenesis the maximum absorption wavelength of galacturonic acid standard solution is 520.89 nm. As shown in FIG. 4, curve B refers to the scanning result of sample from which the sugar is removed by acidic alcohol solution, curve C refers to the scanning result of sample from which the sugar is removed by alcohol solution. According to FIG. 4, results of both pre-treatment methods demonstrate that, after chromogenesis, maximum absorption wavelengths of pectin component in both test solution are approximately 510 nm, more specifically, 507.90 nm and 508.03 nm respectively. In addition, when wavelength is fluctuated at a level of 5 nm within the range of 490 nm-540 nm, the fluctuation of the chromogenic peak is at a level of less than 5%. Therefore, suitable wavelength scope for determination is 490 nm-540 nm, and preferably, 510 nm-520 nm.

3.I Interference to Determination Result Caused by Sugar Content

After being determined, the sugar content in the test solution, i.e., the extract with extracted pectin, is less than 2.5%. The program and result of are as follow:

Experimental methods: two samples, flue-cured tobacco (1#) and burley tobacco (2#), are employed and treated according to the method of the present invention to prepare the test solutions. The total contents of water-soluble sugar in said test solutions are determined by continuous flow analysis.

TABLE 2

Determination results of sugar contents in acidolyzed samples

| Sample | Treated by acidic alcohol solution (the total sugar content is calculated on the basis of glucose) | |
|---|---|---|
| | Total sugar concentration, mg/L | Total sugar content, % |
| 1# | 9.32 | 2.33 |
| 2# | 8.28 | 2.07 |

According to the above data, the sugar contents in the test solutions are relatively low, and the interference therefrom to the pectin determination results is verified by the following experiment.

Experimental methods: in order to determine the interferences caused by sugar components to the continuous flow analysis of the present invention, various testing sugar solution sat a concentration of 20-100 mg/L are prepared (such concentration is 2-10 times of sugar as those in the real sample, and is 0.5-2.5 times if compared with pectin content in the real sample), and determined according to the method described in the previous embodiment. Determination results are shown in Table 3.

Note: According to the sample pretreatment method, 0.1 g powdered tobacco sample is weighed and extracted. The extract is diluted to the metered volume of 250 mL. When the pectin content is 10%, the pectin concentration is 40 mg/L; when the total sugar content is 2.5%, the total sugar concentration is 10 mg/L.

TABLE 3

Determination results of different sugar components obtained by p-hydroxydiphenyl method (calculated on the basis of galacturonic acid)

| | Erroneous result, mistaken judged as pectin, % | |
|---|---|---|
| Sugar type (content mg/L) | First determination result, % | Second determination result, % |
| Arabinose (20) | 0.42 | 0.78 |
| Arabinose (40) | 0.88 | 0.05 |
| Arabinose (60) | 0.94 | 0.99 |
| Arabinose (80) | 0.73 | 0.65 |
| Arabinose (100) | 0.36 | 0.49 |
| Fructose (20) | 0.09 | 0.14 |
| Fructose (40) | 0.24 | 0.68 |
| Fructose (60) | 0.28 | 0.65 |
| Fructose (80) | 0.39 | 0.34 |
| Fructose (100) | 0.29 | 0.51 |
| Glucose (20) | 0.22 | 0.32 |
| Glucose (40) | 0.79 | 0.18 |
| Glucose (60) | 0.04 | 0.15 |
| Glucose (80) | 1.01 | 0.57 |
| Glucose (100) | 1.30 | 0.94 |
| Sucrose (20) | 0.06 | 0.03 |
| Sucrose (40) | 0.02 | 0.02 |
| Sucrose (60) | 0.48 | 0.48 |
| Sucrose (80) | 0.57 | 0.43 |
| Sucrose (100) | 0.91 | 0.49 |
| Galactose (20) | 0.63 | 0.40 |
| Galactose (40) | −0.37 | −0.56 |
| Galactose (60) | −0.48 | 0.20 |
| Galactose (80) | −0.36 | 0.73 |
| Galactose (100) | −0.26 | 0.74 |
| Lactose (40) | −0.87 | −0.74 |
| Lactose (60) | −0.85 | −0.64 |
| Lactose (80) | −1.26 | −1.30 |
| Lactose (100) | −1.01 | −1.49 |
| Rhamnose (20) | −0.76 | 0.21 |
| Rhamnose (40) | −1.58 | −1.14 |
| Rhamnose (60) | −0.79 | −0.28 |
| Rhamnose (80) | −1.02 | −0.82 |
| Rhamnose (100) | −1.52 | −1.28 |

Note:
As the peak heights of components after chromogenesis are very low, that are, much lower than the peak height of standard solution at minimum concentration, and is close to the baseline, determination results are of great fluctuation.

From the data in Table 3, either for monosaccharides such as arabinose, fructose, glucose, galactose, rhamnose, and the like, or for disaccharides such as sucrose, lactose, and the like, even if the concentration of sugar in the test sample is increased to 2-10 times as high as those in normal cases, the chances of erroneous result of which the sugar is mistaken judged as pectin, is very low. Therefore, in terms of pretreatment method and chromogenic condition in the present invention, the sugar components result in little interference to the pectin determination results during the continuous flow determination step. (However, it is also indicated that the treatment of sugar removal must be carried out, because without sugar removal, the sugar content in tobacco sample is not 2.33%, but 20% or even 30%, 40%—since acid hydrolysis is applied, the content of extracted sugar is higher than that of water-soluble sugar.)

4. Selection of Parameters in the Process of Continuous Flow Determination in the Present Invention Basic determination process in this experiment are as follows:

1) The flow of test sample (test solution) is 1.0 mL/min, and total flow of sulphuric acid is 1.8 mL/min, that is, the flow sulphuric acid to sample ratio is 18:1;

2) The heating temperature is 98° C., the helix tube for heating is of 35 turns (generally the heating tube is of 35 or 64 turns; if other heating tube with different turns is needed, then is should be custom-made);

3) The cooling tube is of 30 turns.

In the following experiments concerning different individual items, only the condition relating to the testing item is changed, the other conditions remain the same.

(1). Selection of Flow Ratio

Figure 5:
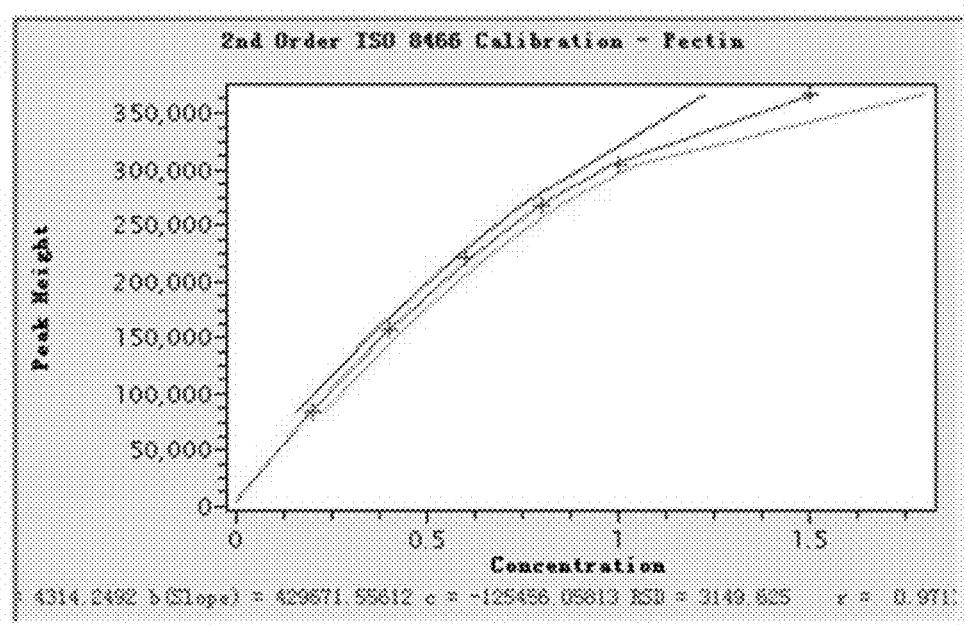
Figure 6:
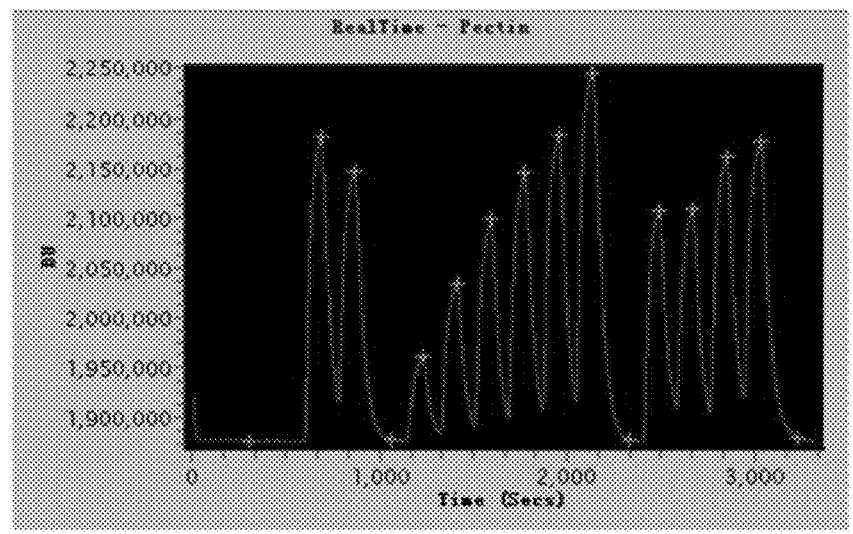
FIG. 6 refers to the first standard curve drawing.
Figure 7:
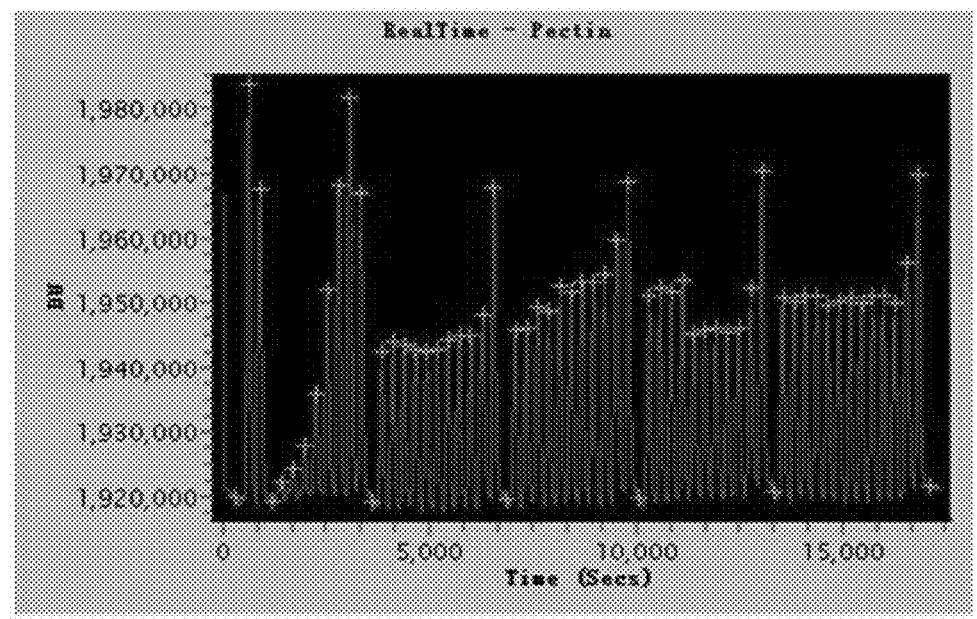
FIG. 7 refers to the second absorbance spectrum scanned by analyzer.
Figure 8:
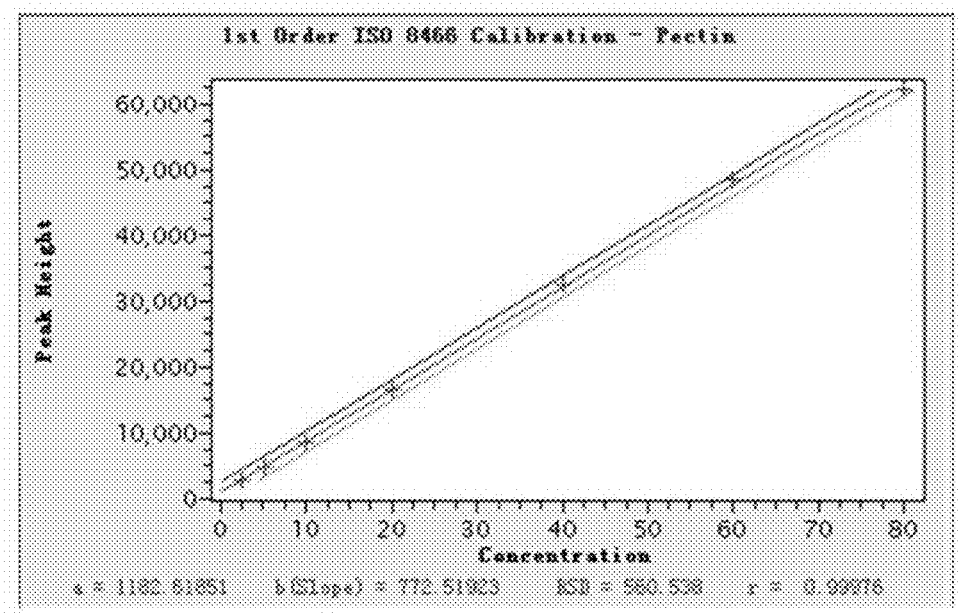
FIG. 8 refers to the second standard curve drawing.

The ratio of the sulfuric acid flow to the test sample flow is adjusted by adjusting the numbers of sulphuric acid pipeline and the flow therein as well as adjusting the flow in sample injection pipeline. The total flow of sulphuric acid is maintained at 3.0 mL/min, the flow in the test sample pipeline is adjusted to 0.32, 0.23, and 0.10 mL/min; the flow in the test sample pipeline is maintained at the range of 0.10-0.23 mL/min, the total flow of sulphuric acid is adjusted to be 2.0, 1.8, and 1.6 mL/min. Determination results are shown in Table 4, wherein when the flow ratio is 13.0:1, the absorbance spectrum scanned by the analyzer and the standard curve drawing are shown in FIG. 5 and FIG. 6, respectively; when the flow ratio is 18.0:1, the absorbance spectrum scanned by analyzer and the standard curve drawing are shown in FIG. 7 and FIG. 8, respectively.

TABLE 4

The correlation coefficients R of standard curves under different flow condition of sulphuric acid

| Items | Determination results | | | | | |
|---|---|---|---|---|---|---|
| Ratio of the sulfuric acid flow to the test sample flow | 9.4:1 | 13.0:1 | 30.0:1 | 20.0:1 | 18.0:1 | 16.0:1 |
| Determination result of sample, % | 7.35 | 9.87 | 9.94 | 10.21 | 10.18 | 9.98 |
| Correlation coefficient R of standard curve | 0.8926 | 0.9713 | 0.9995 | 0.9997 | 0.9998 | 0.9991 |

From table 4 as well as FIG. 5 and FIG. 6, it can be seen that when the ratio of the sulfuric acid flow to the test sample flow is relatively small, the peak corresponding to a lower pectin content has a higher peak height, whereas the peak corresponding to a higher pectin content has a lower peak height, resulting in a lower test result of pectin content. It is indicated that the chromogenic reaction of pectin components is not sufficiently completed, affecting the accuracy of the determination. While if the ratio of the sulfuric acid flow to the test sample flow is appropriate, the correlation coefficient R of standard curve is able to achieve the level of more than 0.999 (see FIG. 7 and FIG. 8). Therefore, the appropriate flow ratio is 13:1-30:1, or preferably 16:1-20:1.

(2). Selection of Heating Temperature

By adjusting the temperature of heater, and comparing the determined values concerning pectin content, the results are shown in Table 5.

TABLE 5

The determination results of pectin under different heating conditions

| Items | Determination results | | | |
|---|---|---|---|---|
| Temperatures of the heater, ° C. | 70 | 80 | 90 | 98 |
| Measured value of pectin content, % | 6.75 | 8.89 | 10.11 | 10.18 |

Note:
Maximum temperature is lower than 100° C., because there will be disordered bubbles emerging in the helix tube, making the absorbance scanning image disordered, and thus will cause unstable result.

From the data in Table 5, it can be seen that when the temperature of the reaction between sulfuric acid and sample is relatively low, determination result will be correspondingly lower. It is indicated that the reaction of the sample is not sufficiently completed. Accordingly, the appropriate heating temperature is 90° C.-99° C., or preferably 98° C. (because if the temperature reaches 100° C., disordered bubbles will emerge in the pipeline at some time).

(3). Selection of Turns of Helix Tube for Cooling (Cooling Time)

TABLE 6

The determination results of pectin under different cooling conditions

| Items | Determination results | | | | | |
|---|---|---|---|---|---|---|
| Turns of cooling tubes | 10 | 20 | 30 | 40 | 50 | 60 |
| Outlet temperature of cooling tubes, ° C. | 32 | 26 | 24 | 23 | 23 | 22 |

From the data in Table 6, it can be seen that when the turns of cooling tube reaches to 30 turns, it is already able to decrease the temperature of reacted sample to around the room temperature, and thus prevent the colorimetric cuvette and the waste liquid tube from damaging. But the turns of cooling tube should not be too much, because it is found that when the turns of cooling tube reaches 60 turns, although the determination results are not significantly changed, the peak heights of samples exhibit more obvious decline. It is indicated that this condition goes beyond the time scope suitable for the chromogenic reaction of the sample. Therefore, appropriate turns of cooling tubes are 20-50 turns.

5. Recovery of the Determination Method of the Present Invention

In accordance with the methods described in the aforementioned embodiments, plant samples having different pectin contents are treated to obtain the test solutions. The test solutions are drawn into the continuous flow analyzer, reacted with sulfuric acid solution containing sodium tetraborate decahydrate, decomposed and converted into furfurine derivatives, which is further reacted with the chromogenic reagent (p-hydroxydiphenyl solution), and then determined at a wavelength of 520 nm. The flow chart of the analyzer is shown in FIG. 2:

TABLE 7

The R value of standard curves under the condition of different sulphuric acid flows

| The additive amount of pectin, mg | The amount corresponding to galacturonic acid, mg | Value, mg | Recovery, % |
|---|---|---|---|
| 0 | 0 | 10.2 | — |
| 8.17 | 6.21 | 16.8 | 106.3 |
| 18.08 | 13.74 | 24.0 | 100.4 |
| 23.75 | 18.06 | 28.6 | 101.9 |

Note:
The data in the table are the mean values of triplicate treatments.

From Table 7, it can be seen that the recovery of the present determination method is 100%-106%, which is able to meet the requirements of quantitative determination.

6. Contrasted Experiment

Experimental program: two methods, the gravimetric method as in the prior art and the determination method of the present invention, are employed to determine the pectin contents in two identical tobacco samples. Differences between the determination results are compared. The results are shown in Table 8.

The gravimetric method: 1 g powdered tobacco sample is accurately weighed (accurate to 0.0001 g), and heated to reflux for 20 min in 200 mL anhydrous ethanol, followed by a suction filtration, the residue is heated to reflux for 20 min in 100 mL 80% ethanol, and then suction filtered. The resulting residue is added into 200 mL sulfuric acid solution (pH=2), extracted at 90° C. for 1.5 h, followed by a filtration when the temperature is still high. The residue is washed with distilled water for three times, and the extract is concentrated and then precipitated in ethanol. The precipitate is filtered, dried and weighed for the weight of precipitate.

Determination method of the present invention: 1 g powdered tobacco sample is accurately weighed (accurate to 0.0001 g), and determined in accordance with the methods described in the aforementioned embodiments.

TABLE 8

Pectin content results of different determination methods

| Sample | Gravimetric method, % | Determination method of the present invention, % |
|---|---|---|
| 1# | 12.60 | 8.74 |
| 2# | 12.54 | 8.39 |

From the data in Table 8, it can be concluded that: the values of the gravimetric method are higher than those of the determination method in the present invention. This is because, when employing the gravimetric method, neutral sugars and alpha-L-(1→2) rhamnoses on the branched chains, as well as methylated groups and acetylated groups, are simultaneously precipitated, and the pectin determined is not only those polymerized from galacturonic acid. Therefore, the value determined by this method will be higher than the method that cumulates the amount of galacturonic acid. Therefore, the values of the gravimetric method are higher than those of the continuous flow analysis method, and the results of the gravimetric method could not imply the galacturonic acid content in the sample.

Previously provided are only preferred embodiments of the present invention, it should be noted that the above preferred embodiment should not be regarded as any limitation to the present invention, and the protective scope of the present invention should be defined according to the claims. Without departing from the spirit and scope of the present invention, people skilled in the art can make various improvements and modifications, which should also be regarded as within the protection scope of the present invention.

The invention claimed is:

1. A method for determining pectin content in a plant sample, wherein said method comprises steps of:
   1) adding an acidic alcohol solution to the plant sample, followed by a heating in a water bath and then a first filtration; wherein the acidic alcohol solution has an alcohol concentration of 60%-80% (v/v) and a hydrogen ion concentration of 0.005 mol/L-0.02 mol/L;
   2) soaking a filtered residue obtained from the first filtration with an acid solution, followed by a heating in a water bath and then a second filtration, then bringing to volume after cooling, obtaining a filtrate for later use; wherein the acidic solution is 0.05-0.1 N acid solution;
   3) adding an acetic acid/sodium acetate buffer solution to treat a filtered residue obtained from the second filtration, then adding a pectinase solution and heating the resulting mixture under vibration in a water bath, followed by a third filtration to obtain a filtrate for later use;
   4) adding an acetic acid/sodium acetate buffer solution and a pectinase solution in sequence to the filtrate obtained in step 2) and heating the resulting mixture under vibration in a water bath to obtain an enzymatic hydrolysate, then adding the filtrate obtained in step 3) to the enzymatic hydrolysate followed by bringing to volume, obtaining a test solution; and
   5) drawing the test solution into a continuous flow analyzer to perform analysis, wherein the test solution is reacted with a strong-acid decomposing reagent drawn into the continuous flow analyzer, to form furfurine derivatives, which is further reacted with an chromogenic reagent, followed by a determination under a wavelength of 490-540 nm.

2. The method according to claim 1, wherein said acidic alcohol solution is added at a ratio of 50 mL-200 mL acidic alcohol solution: 1 g sample.

3. The method according to claim 1, wherein the heating under vibration in a water bath in step 1) is conducted under 80° C.-100° C. for 10 min-1 h.

4. The method according to claim 1, the heating to reflux in a water bath is conducted under 80° C.-100° C. for 30 min-2 h; the volume of the filtrate after bringing to volume is controlled at 200 mL-250 mL for every 1 g plant sample.

5. The method according to claim 1, wherein in step 3), the acetic acid/sodium acetate buffer solution and the pectinase solution are added at a ratios of 1 g plant sample: 15 mL-20 mL buffer solution: 1 mL-2 mL pecinase solution; wherein the enzymatic activity per 1 mL pectinase solution is above 300 enzymatic active unit; the heating under vibration in a water bath is conducted under 40° C.-60° C. for 1 h-2 h.

6. The method according to claim 1, wherein in step 4), every 1 mL filtrate is added with 15-20 mL buffer solution and 1-2 mL pectinase solution; wherein the enzymatic activity per 1 mL pectinase solution is above 300 enzymatic active unit; the heating under vibration in a water bath is conducted under 40° C.-60° C. for 1 h-2 h.

7. The method according to claim 1, wherein in step 5), the test solution is mixed with the strong-acid decomposing reagent via a helix tube and is heated during reaction with the strong-acid decomposing reagent, followed by a cooling.

8. The method according to claim 1, wherein the plant sample is powdery.

9. The method according to claim 1, wherein the plant sample in step 1) is added with an acidic alcohol solution and stirred to become slurry before heating to reflux in a water bath, if said plant sample has a large volume.

10. The method according to claim 1, wherein said the chromogenic reagent is p-hydroxydiphenyl solution, wherein said p-hydroxydiphenyl solution is formed by components at a ratio of 1000 mL water:300-500 mg p-hydroxydiphenyl:3 g-5 g sodium hydroxide.

11. The method according to claim 1, wherein the strong-acid decomposing reagent is sulfuric acid containing sodium tetraborate, wherein 3 g-6 g sodium tetraborate is dissolved in 1000 mL sulphuric acid solution at a concentration of 92%-99% concentrated.

12. The method according to claim 7, wherein the test solution and the strong-acid decomposing reagent is reacted at a temperature in the range of 90° C.-99° C.

13. The method according to claim 7, wherein the cooling is performed in the cooling tube with 20 turns-50 turns.

14. The method according to claim 1, wherein the pectinase solution in step 3) and/or step 4) are/is at a volume concentration of 300 u/mL-600 u/mL.

* * * * *